United States Patent
Ruzzo et al.

(10) Patent No.: US 7,229,661 B2
(45) Date of Patent: Jun. 12, 2007

(54) METHODS FOR PREPARING AND TESTING A THERMAL-SPRAY COATED SUBSTRATE

(75) Inventors: Patsy Augestine Ruzzo, Clearwater, FL (US); Matthew Stewart, Cincinnati, OH (US); Anthony William Mellors, West Chester, OH (US)

(73) Assignee: General Electric Company, Schenectady NY ( * ) Notice: Subject to any disclaimer, the term of this patent is extended or adjusted under 35 U.S.C. 154(b) by 0 days.

(21) Appl. No.: 11/469,711

(22) Filed: Sep. 1, 2006

(65) Prior Publication Data

US 2007/0077362 A1    Apr. 5, 2007

Related U.S. Application Data

(62) Division of application No. 10/761,857, filed on Jan. 21, 2004, now Pat. No. 7,126,329.

(51) Int. Cl.
*B05D 1/02* (2006.01)
*C23C 16/44* (2006.01)
*G01R 33/12* (2006.01)

(52) U.S. Cl. .................... 427/8; 427/455; 427/456; 324/228

(58) Field of Classification Search .............. 427/8–10, 427/455–456; 324/228
See application file for complete search history.

(56) References Cited

U.S. PATENT DOCUMENTS

| 5,956,845 A | 9/1999 | Arnold |
| 6,049,978 A | 4/2000 | Arnold |
| 6,071,628 A | 6/2000 | Seals et al. |
| 6,368,672 B1 | 4/2002 | Thompson et al. |
| 6,398,103 B2 | 6/2002 | Hasz et al. |
| 6,451,454 B1 | 9/2002 | Hasz et al. |
| 6,955,308 B2 | 10/2005 | Segrest et al. |
| 7,043,819 B1 | 5/2006 | Arnold |
| 7,126,329 B2 | 10/2006 | Ruzzo et al. |
| 7,150,921 B2 | 12/2006 | Nelson et al. |

*Primary Examiner*—Bot LeDynh
(74) *Attorney, Agent, or Firm*—William Scott Andes; Armstrong Teasdale LLP

(57) ABSTRACT

A method for fabricating and testing an article having a thermal-spray coating thereon. The method includes providing a substrate article having a surface, thermally spraying a coating material onto the surface of the substrate article, wherein a surface of contact between the coating material and the substrate article is a bondline, and nondestructively testing the coated article. Nondestructively testing includes generating an eddy current in the coated article, measuring the eddy current in the coated article, and evaluating a near-bondline region of the coated article located adjacent to the bondline using the measured eddy current.

10 Claims, 5 Drawing Sheets

METHODS FOR PREPARING AND TESTING A THERMAL-SPRAY COATED SUBSTRATE

CROSS-REFERENCE TO RELATED APPLICATIONS

This application is a divisional of U.S. patent application Ser. No. 10/761,857, filed Jan. 21, 2004 now U.S. Pat. No. 7,126,329, which is hereby incorporated in its entirety by reference and is assigned to assignee of the present invention.

BACKGROUND OF THE INVENTION

This invention relates generally to the preparation of substrates having a thermal-spray coating thereon, and more particularly to methods of testing of the integrity of a bond between the thermal-spray coating and the substrate.

At least some known metallic coatings are applied to substrates using a thermal-spray process in which a coating material, usually provided in a powder or wire form, is heated to an elevated temperature in a spray device. The coating material may be fully melted to form liquid droplets, may be partially melted to form semiplastic particles, or may remain formed as solid powder particles. The coating material is discharged from the spray device at a high velocity and towards a substrate surface. The sprayed material is deposited on the surface and, to the extent that it is liquid, solidifies. More specifically, droplets and particles impact the surface at a relatively high velocity, and are substantially flattened against the surface. The deposition continues until the solidified coating has reached a desired thickness.

The thermal-spray process is highly versatile and may be used with a wide variety of compositions and substrate articles. For example, the thermal-spray process may be used to deposit a coating on an article that has been partially worn away during prior service, wherein the coating has substantially the same composition as the substrate article. In another example, the thermal-spray process is used to deposit a wear-resistant coating across a surface, wherein the coating has a different composition than the substrate article and is more wear-resistant than the substrate article. In yet another example, the thermal-spray process may be used to deposit a wearing or abradable coating across a surface, wherein the coating has a different composition than the substrate article and is less wear resistant than the substrate article. Moreover, the thermal-spray process may be used to coat irregular and complexly shaped article substrates.

Generally, to be effective, the thermally sprayed coating must adhere at a bondline to the entire surface to which it is applied with a good mechanical bond. Accordingly, delaminations of the coating from the substrate may enable the coating to separate from the substrate. In some more-demanding applications, the coating must further be metallurgically bonded to the substrate.

At least one known method to determine the bonding strength of the bonding of the sprayed coating to the substrate requires destructive sectioning of the coated article and metallurgical inspection of the bondline region. This method is normally used to establish process parameters that achieve a good bonded coating, and then the same process parameters are duplicated in the production coating operations. Because the thermal-spray process is so versatile, it may be difficult to perform destructive testing over the entire range of possible types of coatings and configurations of substrate articles. Moreover, even if a process is deemed through the destructive testing process, relatively minor variations in production parameters may lead to unacceptable bondline structures in the production articles. Another problem with the use of test articles is the test articles may behave differently than the production articles. Additionally, post-coating operations such as heat treating and machining may introduce bondline defects to initially defect-free bondlines.

BRIEF DESCRIPTION OF THE INVENTION

In one aspect, a method for fabricating and testing an article having a thermal-spray coating thereon is provided. The method includes providing a substrate article having a surface, thermally spraying a coating material onto the surface of the substrate article, wherein a surface of contact between the coating material and the substrate article is a bondline, and nondestructively testing the coated article. Nondestructively testing includes generating an eddy current in the coated article, measuring the eddy current in the coated article, and evaluating a near-bondline region of the coated article located adjacent to the bondline using the measured eddy current.

In another aspect, a system for testing an article having a thermal-spray coating thereon is provided. The system includes a turntable having a thermally coated substrate article positioned thereon, an eddy current probe operatively coupled to the substrate article, the eddy current probe configured to generate an eddy current within the coated substrate article and measure the eddy current within the coated substrate article, and a computer configured to determine a near-bondline region of the coated article located adjacent to a bondline using the measured eddy current.

DETAILED DESCRIPTION OF THE INVENTION

Figure 1:
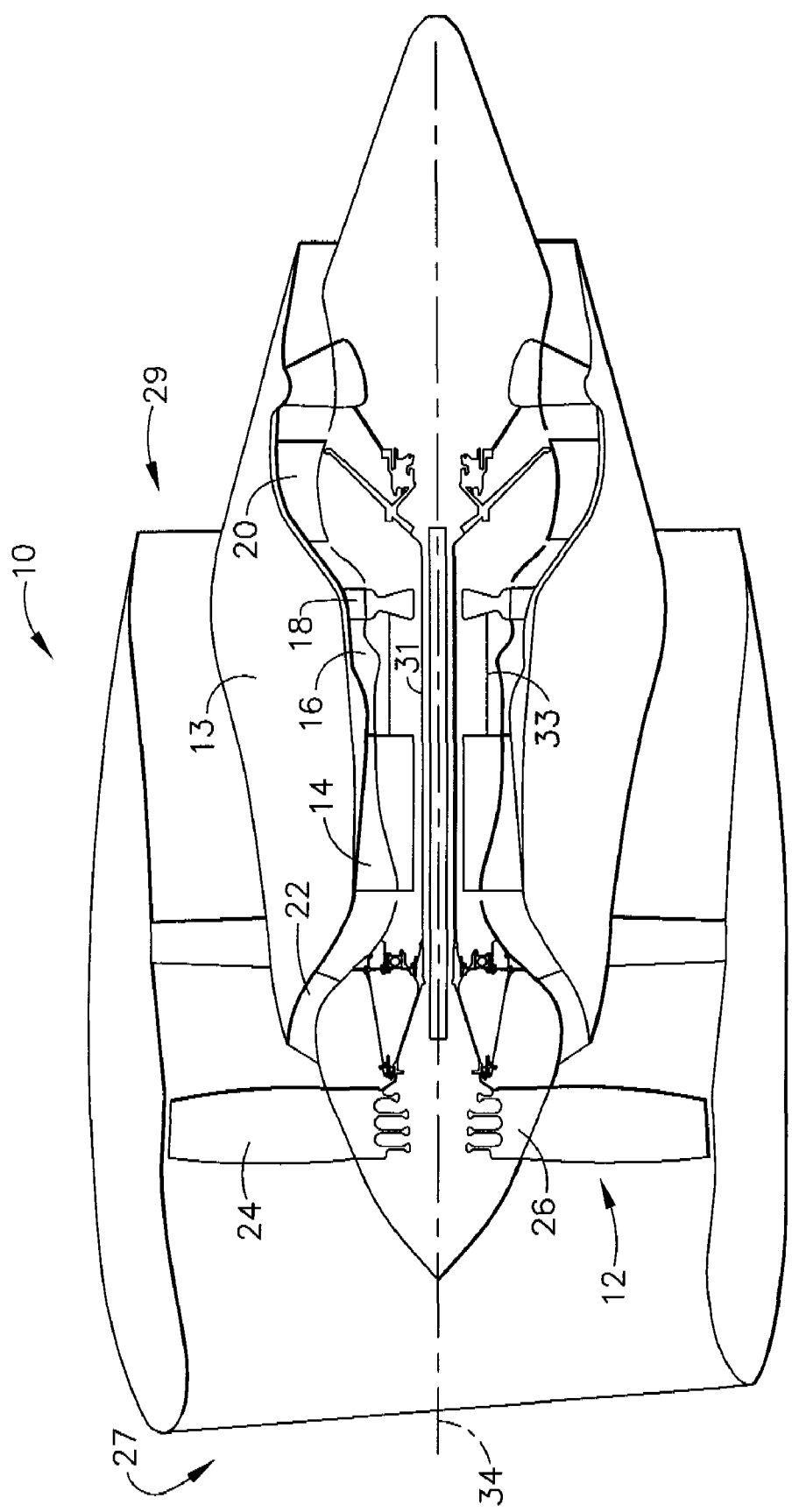
FIG. 1 is a schematic illustration of an exemplary gas turbine engine.

FIG. 1 is a schematic illustration of a gas turbine engine 10 including a fan assembly 12 and a core engine 13 including a high pressure compressor 14, and a combustor 16. Engine 10 also includes a high pressure turbine 18, a low pressure turbine 20, and a booster 22. Fan assembly 12 includes an array of fan blades 24 extending radially outward from a rotor disc 26. Engine 10 has an intake side 27 and an exhaust side 29. In one embodiment, the gas turbine engine is a CF6-50 available from General Electric Company, Cincinnati, Ohio. Fan assembly 12 and turbine 20 are coupled by a first rotor shaft 31, and compressor 14 and turbine 18 are coupled by a second rotor shaft 33.

During operation, air flows axially through fan assembly 12, in a direction that is substantially parallel to a central axis 34 extending through engine 10, and compressed air is supplied to high pressure compressor 14. The highly compressed air is delivered to combustor 16. Airflow (not shown in FIG. 1) from combustor 16 drives turbines 18 and 20, and turbine 20 drives fan assembly 12 by way of shaft 31.

Figure 2:
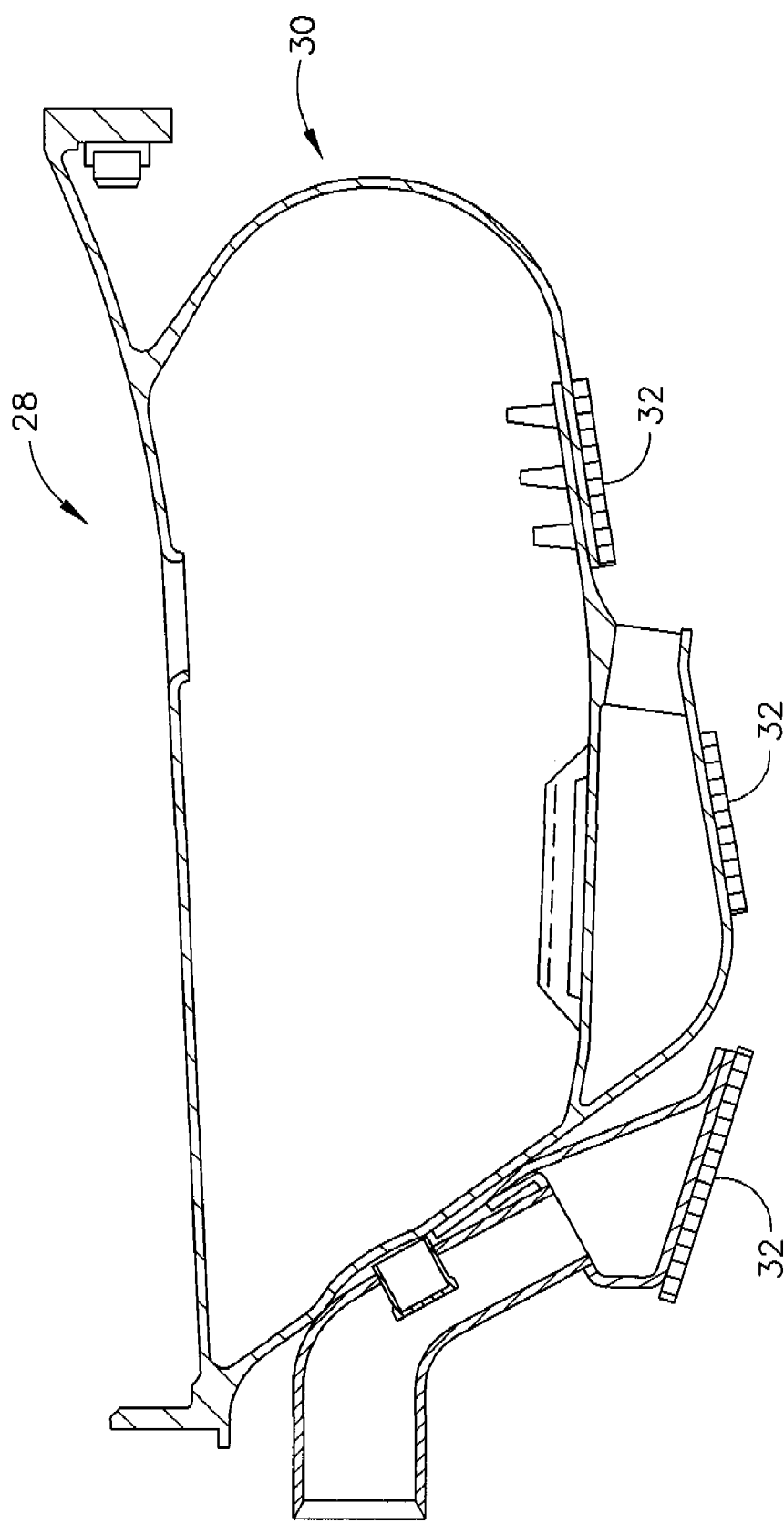
FIG. 2 is a perspective view of a turbine stationary seal used with the gas turbine engine shown in FIG. 1

FIG. 2 is a perspective view of an article 28 to be tested. In the exemplary embodiment, article 28 is a stationary seal 30 that includes a plurality of honeycomb land surfaces 32. For example, and in the exemplary embodiment, stationary seal 30 is a pressure balance seal that can be used with gas turbine engine 10 (shown in FIG. 1).

Although the methods herein are described with respect to a stationary seal, it should be appreciated that the methods can be applied to a wide variety of articles. For example, article 28 may be of any operable shape, size, and configuration. Examples of substrate articles of interest include areas of components of gas turbine engines such as seals and flanges, as well other types of articles. The substrate article may be made of any operable base material. Examples of operable base materials include nickel-base alloys, which have more nickel by weight than any other element; cobalt-base alloys, which have more cobalt by weight than any other element; titanium-base alloys, which have more titanium by weight than any other element; iron-base alloys, which have more iron by weight than any other element; and aluminum-base alloys, which have more aluminum by weight than any other element. An example of a nickel-base alloy of particular interest is Alloy 718, having a specification composition, in weight percent, of from approximately 50.0% to approximately 55.0% nickel, from approximately 17.0% to approximately 21.0% chromium, from approximately 4.75.0% to approximately 5.50% columbium plus tantalum, from approximately 2.8% to approximately 3.3% molybdenum, from approximately 0.65% to approximately 1.15% titanium, from approximately 0.20% to approximately 0.80% aluminum, approximately 1.0% percent cobalt, and a balance of iron totaling 100% by weight. Small amounts of other elements such as carbon, manganese, silicon, phosphorus, sulfur, boron, copper, lead, bismuth, and selenium may also be present. These substrate articles and compositions are presented by way of examples of preferred embodiments, and not by way of limitation.

In one embodiment, coating 40 is a thermal barrier coating such as, but not limited to, a Nickel Chromium Aluminum (NiCrAl) coating having a nominal composition range, in weight percent, of from approximately 4.5% to approximately 7.5% percent aluminum, from approximately 15.5% to approximately 20.5% chromium, approximately 3.0% manganese, approximately 1.0% iron, approximately 0.3% carbon, approximately 2.0% silicon, approximately 3.5% of other elements, and approximately 70.0% nickel. In the exemplary embodiment, coating 40 is between approximately 0.002 inch and approximately 0.150 inch in thickness and may be applied to stationary seal 30 using a quantity of thermal spray techniques such as, but not limited to, high velocity oxyfuel spray (HVOF), air plasma spray (APS), low-pressure-plasma spray (LPPS), electric wire arc spray, and combustion wire or powder spray. After coating 40 is applied to a surface 64 of article 28, a heat treatment operation is performed to facilitate diffusing coating 40 into article 28. Coating 40 is then non-destructively tested to determine if any bondline faults exist between coating 40 and surface 64 of article 28. More specifically, a wide variety of factors, such as the shape of article 28, i.e. stationary seal 30, the base material of article 28, the coating material, i.e. coating 40, and variations in operating parameters may result in near-bondline flaws between article 28 and coating 40. Such flaws may cause thermal-spray coating 40 to perform in an unsatisfactory manner. Therefore article 28 is tested to determine whether such flaws are present in article 28 and when coated article 28 is free of such flaws.

Figure 3:
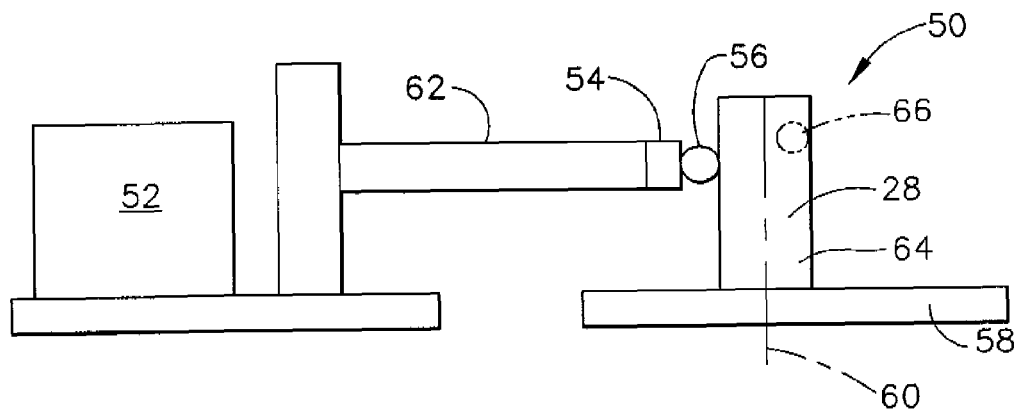
FIG. 3 is a block diagram of a system for testing an article having a thermal-spray coating thereon.
Figure 4:
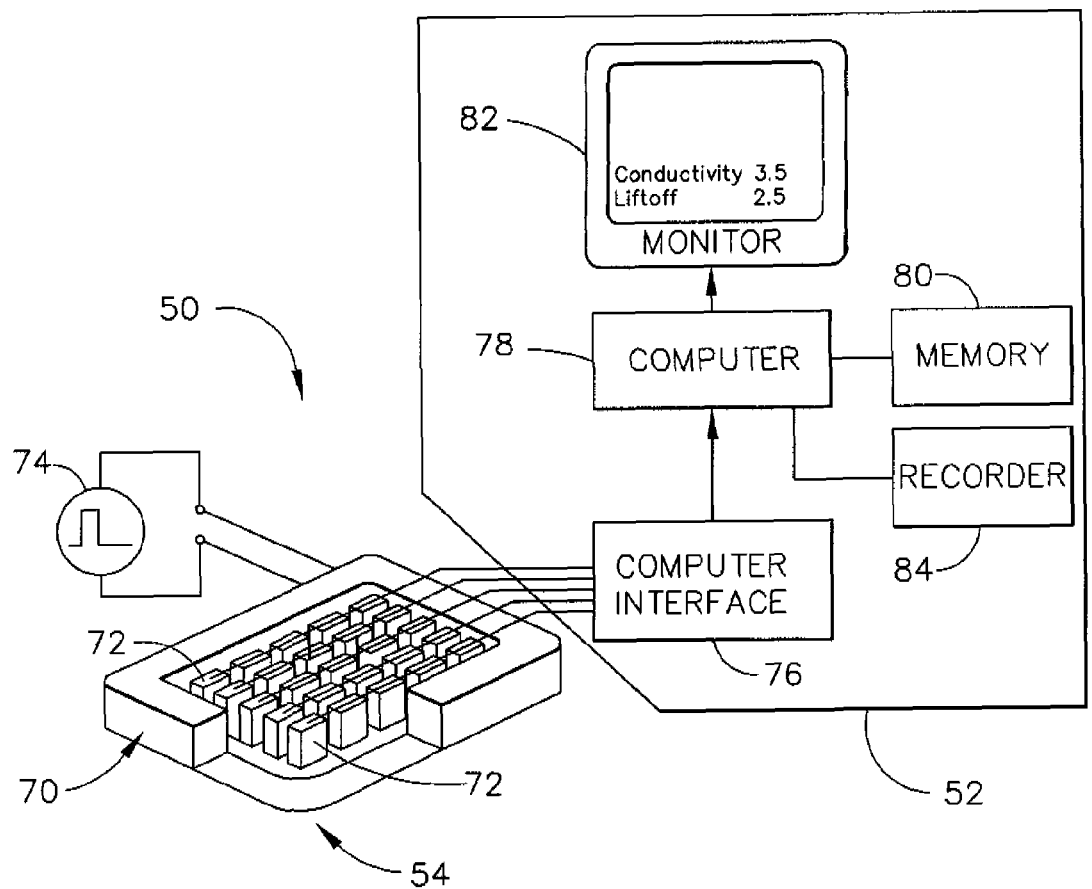
FIG. 4 is an exploded view of the system shown in FIG. 3.

FIG. 3 is a system 50 that may be used to non-destructively test a bondline between a metallic substrate, such as stationary seal 30, and a coating applied to the substrate, such as coating 40. FIG. 4 is a portion of system 50 shown in FIG. 3. In the exemplary embodiment, system 50 is an eddy current inspection system 50 that includes a data acquisition/control system 52, and an eddy current probe 54 having a cam 56. In the exemplary embodiment, eddy current probe 54 is a cam follower probe configured to operate at approximately 500 kiloHertz. Eddy current probe 54 is electrically coupled to data acquisition/control system 50 such that control/data information can be transmitted to/from eddy current probe 54 and data acquisition/control system 52. System 50 also includes a turntable 58 configured to rotate around an axis 60, and a mechanical member 62 such as, but not limited to, a robotic arm slidably coupled to article 28 such as, a portion of turbine stationary seal 30 positioned on turntable 58.

FIG. 4 is an enlarged view of data acquisition/control system 52 and eddy current probe 54 shown in FIG. 3. Although eddy current probe 54 is shown as a two-dimensional sensor array similar to that disclosed in U.S. Patent Publication No. US 2002/0190724 A1 of Ser. No. 09/681,824, filed Jun. 12, 2001 and assigned to General Electric Company, configurations of the present invention do not necessarily require either a two-dimensional sensor array or the two-dimensional capabilities disclosed in that Patent Publication.

Eddy current probe 54 includes a drive coil 70, which is shown partially cut away in FIG. 4 to reveal more details of an included sensor or sensors 72, and a square pulse generator 74. Data acquisition/control system 52 includes a computer interface 76, a computer 78, such as a personal computer with a memory 80, and a monitor 82. Computer 78 executes instructions stored in firmware (not shown). Computer 78 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Drive coil 70 is a multiple turn solenoid that can be of generally rectangular configuration surrounding sensor or sensors 72. Sensors 72 can be located inside or outside as well as above or below drive coil 70. Rectangular drive coil 70 is used to transmit a transient electromagnetic flux into a metallic object under test such as article 28 (shown in FIG. 3). Memory 80 is intended to represent one or more volatile and/or nonvolatile storage facilities not shown separately that are familiar to those skilled in the art. Examples of such storage facilities often used with computer 78 include solid state memory (e.g., random access memory (RAM), read-only memory (ROM), and flash memory), magnetic storage devices (e.g., floppy disks and hard disks), optical storage devices (e.g., CD-ROM, CD-RW, and DVD), and so forth. Memory 80 may be internal to or external to computer 78. Data acquisition/control system 52 also includes a recording device 84 such as, but not limited to, a strip chart recorder, a C-scan, and an electronic recorder, electrically coupled to at least one of computer 78 and eddy current probe 54.

Figure 5:
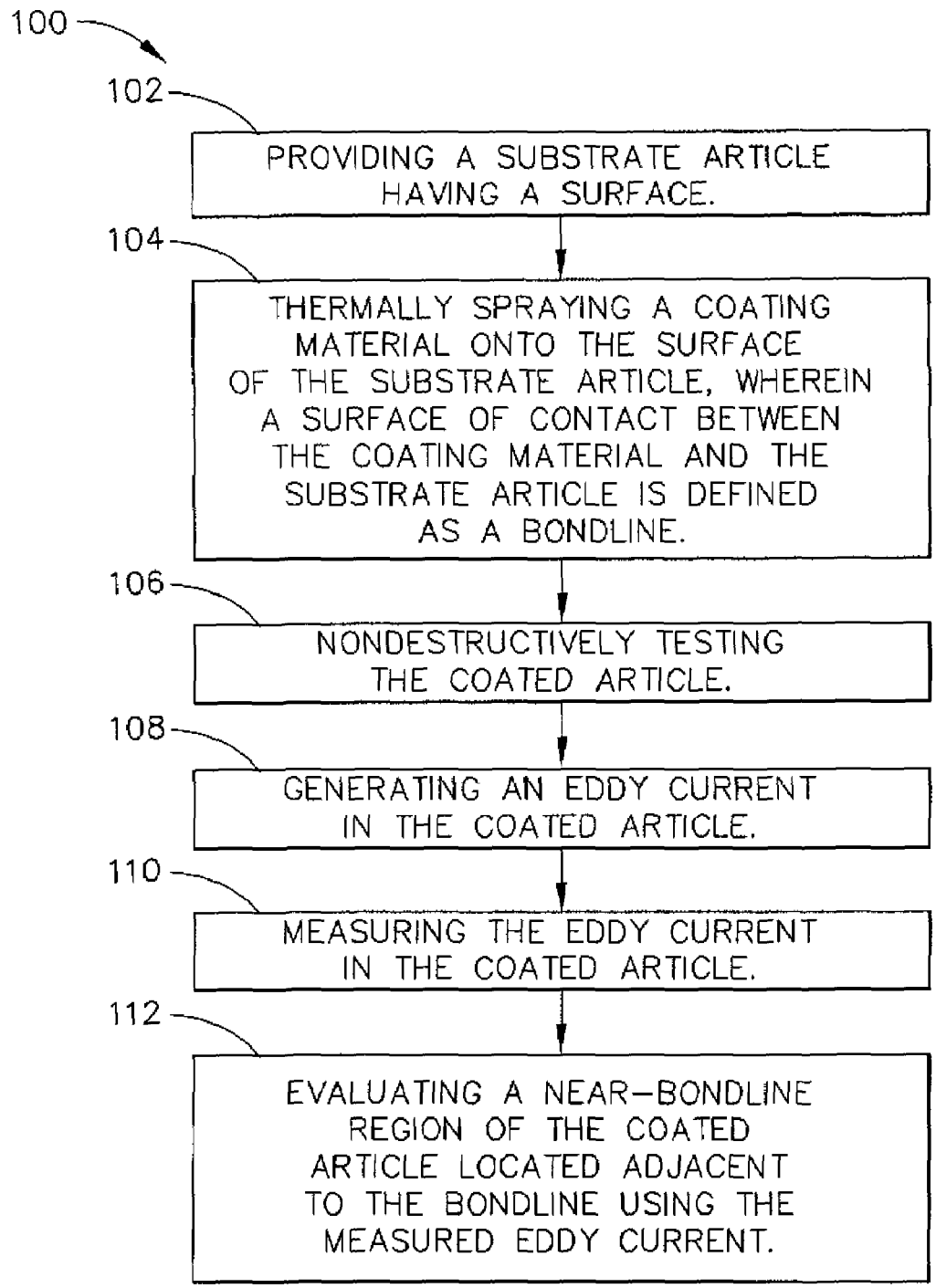
FIG. 5 is of a flowchart illustrating a method for testing an article having a thermal-spray coating thereon.

FIG. 5 is a method 100 for fabricating and testing an article having a thermal-spray coating thereon. Method 100 includes providing 102 a substrate article 28 having a surface 64, and thermally spraying 104 a coating material 40 onto surface 64 of substrate article 28, wherein a surface of contact between coating material 40 and substrate article 28 is defined as a bondline. Coated article 28 is then positioned on turntable 58. Turntable 58 is then energized such that coated article 28 is rotated around axis 60 of turntable 58. Method 100 further includes nondestructively testing 106 coated article 28, wherein nondestructively testing 106 includes generating 108 an eddy current in coated article 28, measuring 110 the eddy current in coated article 28, and evaluating 112 a near-bondline region of coated article 28 located adjacent to the bondline using the measured eddy current.

More specifically, pulse generator 74 is used to excite drive coil 70 with an essentially rectangular-shaped short duration pulse of electrical current while sensors 72 and coil 70 are on or proximate surface 64 of coated article 28. As a result, a pulsed eddy current is generated in coated article 28 under test. Sensor or sensors 72 sense the pulsed eddy current as a voltage. For example, the pulsed eddy current may produce a signal ranging from approximately +500 mV to approximately −500 mV in sensor or sensors 72 for a particular article 28. In the exemplary embodiment, only a signal generated by one sensor 72 is considered for the remainder of this discussion, as a plurality of sensors 72 is not required to practice many configurations of the present invention. Also, sensor 72 may produce either a voltage or a current indicative of the pulsed eddy current. Therefore, "a measured eddy current," as used herein, includes any measured representation of the eddy current, whether the representation is in the form of a voltage, a current, or a digitized value.

Computer interface 76 receives a response signal from sensor 72 and communicates a digitized signal representative of the pulsed eddy current during a measurement window into computer 78. In the exemplary embodiment, the measurement window commences very shortly after the pulse ends. For example, in some configurations, the measurement window begins approximately 10 ms after the pulse ends. In other configurations, the measurement window begins approximately 0.5 ms after the pulse ends. Utilizing a stored program in memory 80, computer 78 parameterizes this digitized signal and applies a transfer function to the parameters to determine at least one measurement/object property. As used herein, a "measurement/object property" is a physical property of the metallic object itself, such as wall thickness, permeability, or conductivity, and/or a property of the measurement, i.e., a physical relationship between the metallic object and the sensor, such as sensor liftoff. A result is then displayed on display 82 and/or saved in memory 80 and/or printed on a printer (not shown in the figures) for later use. In another embodiment, the digitized signal is received at recording device 84 and stored for later use.

Figure 6:
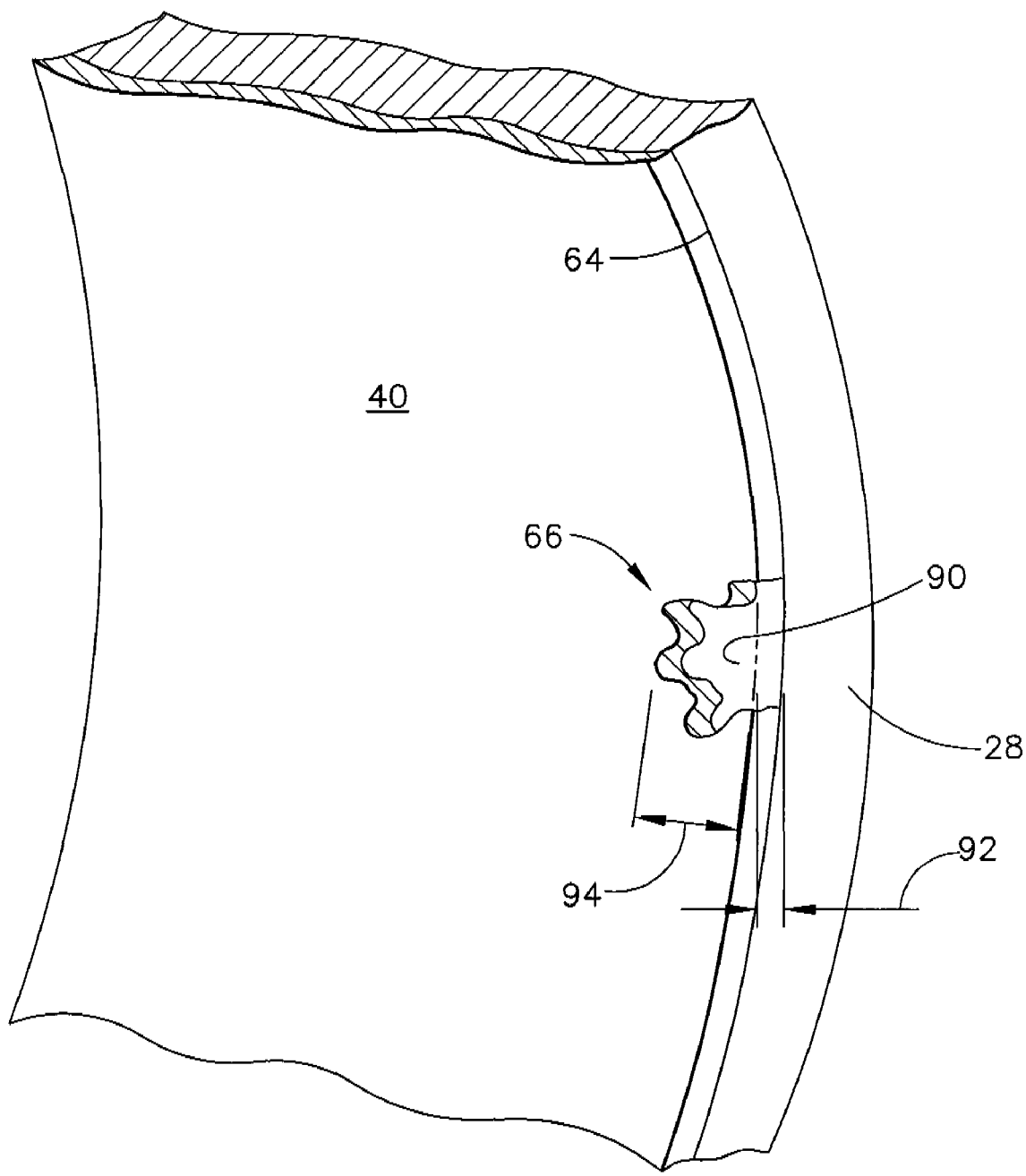
FIG. 6 is a perspective view of an article having a thermal-spray coating thereon.

The received signal is then evaluated 112 to determine whether a near-bondline region 66 is delaminated, exhibits a mechanical bond (with no delamination), or exhibits a metallurgical bond (with no delamination). As used herein, near-bondline region 66 includes, but is not limited to, a flat bottom hole for example, in coating 40. Evaluating 112 includes generating a preferred acceptability criterion. Specifically, and referring to FIG. 6, article 28 is dynamically tested using system 50 as described previously herein. In operation, system 50 is capable of determining a bondline fault region 66 that includes a substantially flat bottom 90 that is approximately 0.020 inches in depth 92, wherein the fault region is approximately 1/32 of an inch in width 94. At least one of computer 78 and recording device 84 is then used to determine whether bondline fault region 66 is within acceptable limits. Any bondline fault region which exceeds the predetermined threshold is then evaluated to determine an actual size.

The above-described methods and system provide a cost-effective and reliable means for facilitating determining near bondline faults in thermal spray coated articles. Although the methods are described with respect to coating and testing an object that includes an approximately cylindrical outer surface, it should be realized that the methods can be used for an article having a complex outer surface. For example, a digital eddy current proximity system may be used to measure the size and depth of a near bondline fault in a turbine seal. The methods described herein may also be used both as a process-development tool to determine the required processing of the thermally sprayed article, and as an acceptance test on production hardware to determine its acceptability. Additionally, using a cam-follower probe that is mounted on a robotic arm facilitates measuring the eddy current automatically, since the cam follower probe is configured to follow any contour automatically, thus enabling testing a wide variety of substrate articles.

Exemplary embodiments of digital eddy current proximity systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method for a substrate article, said method comprising:
   thermally spraying a coating material onto a surface of the substrate article, wherein a surface of contact between the coating material and the substrate article defines a bondline; and
   nondestructively testing the coated article by:
   generating an eddy current in the coated article;
   measuring the eddy current in the coated article; and
   evaluating a near-bondline region of the coated article located adjacent to the bondline using the measured eddy current.

2. A method in accordance with claim 1 wherein thermally spraying a coating material onto a surface comprises coating an external surface of a gas turbine stationary seal.

3. A method in accordance with claim 1 wherein thermally spraying a coating material onto a surface comprises coating a surface of an article fabricated from at least one of a nickel-base alloy and a cobalt-base alloy.

4. A method in accordance with claim 1 further comprising heat treating the substrate article after thermally spraying a coating material onto the surface of the substrate article.

5. A method in accordance with claim 1 wherein thermally spraying a coating material onto the surface of the substrate article further comprises thermally spraying the coating material using at least one of a high velocity oxyfuel spray, an air plasma spray, a low-pressure-plasma spray, an electric wire arc, a combustion wire spray, and a combustion powder spray.

6. A method in accordance with claim 1 wherein thermally spraying a coating material onto the surface of the substrate article further comprises thermally spraying a metallic material onto a substrate of the article.

7. A method in accordance with claim 1 wherein thermally spraying a coating material onto the surface of the substrate article further comprises depositing a layer of coating material onto the surface of the substrate to have a thickness of between approximately 0.002 and 0.150 inches.

8. A method in accordance with claim 1 wherein nondestructively testing the coated article further comprises:
   coupling the coated article on a turntable; and
   inducing an eddy current into the coated article while the turntable is rotating.

9. A method in accordance with claim 1 wherein nondestructively testing the coated article further comprises:
   generating an eddy current in the coated article using a cam follower probe; and
   recording the measured eddy current using at least one of a computer and a recorder.

10. A method in accordance with claim 1 further comprising:
   coupling a cam follower probe to a robotic arm; and
   manipulating the robotic arm such that the cam follower probe generates an eddy current in the coated article.

* * * * *